United States Patent [19]

King et al.

[11] Patent Number: 4,509,944
[45] Date of Patent: Apr. 9, 1985

[54] CATHETER ASSEMBLY

[75] Inventors: Paul E. King, Ware; Harold C. S. Wilson, Croydon, both of England

[73] Assignee: Hinders-Leslies Limited, Great Britain

[21] Appl. No.: 590,191

[22] Filed: Mar. 16, 1984

Related U.S. Application Data

[63] Continuation of Ser. No. 396,717, Jul. 9, 1982, abandoned, which is a continuation of Ser. No. 173,591, Jul. 30, 1980, abandoned.

[30] Foreign Application Priority Data

Aug. 15, 1979 [GB] United Kingdom ................ 7928375

[51] Int. Cl.³ .............................................. A61M 5/00
[52] U.S. Cl. ...................................... 604/53; 604/164; 604/280
[58] Field of Search ...................... 604/44, 51, 53, 164, 604/166, 220

[56] References Cited

U.S. PATENT DOCUMENTS

| 3,506,007 | 4/1970 | Henkin ................................ 604/51 |
| 4,016,789 | 4/1977 | Mellor ............................. 604/44 X |
| 4,096,860 | 6/1978 | McLaughlin ........................ 604/44 |
| 4,205,675 | 6/1980 | Vaillancourt ....................... 604/53 |

FOREIGN PATENT DOCUMENTS 1064445  12/1953  France ................................ 604/51

Primary Examiner—Stephen C. Pellegrino
Attorney, Agent, or Firm—Jacobs & Jacobs

[57] ABSTRACT

The present invention provides a catheter assembly which comprises catheter tubing, a hollow needle and a guide member with a longitudinal bore there through for aiding insertion of the hollow needle into the catheter, which catheter assembly is characterized in that the longitudinal bore in the guide member has a narrower portion and a communicating broader portion, the narrower portion being adapted to receive in close fit the hollow needle and the broader portion being adapted to receive in close fit the catheter; whereby in use the catheter tubing may be positioned for insertion of the hollow needle.

3 Claims, 12 Drawing Figures

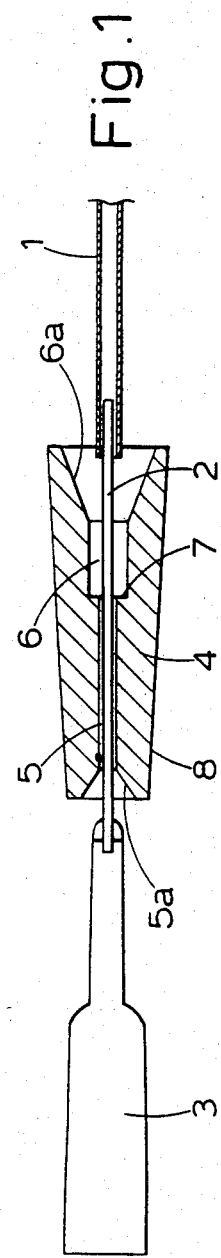
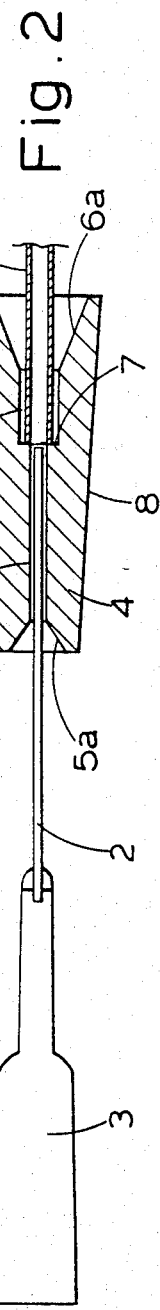
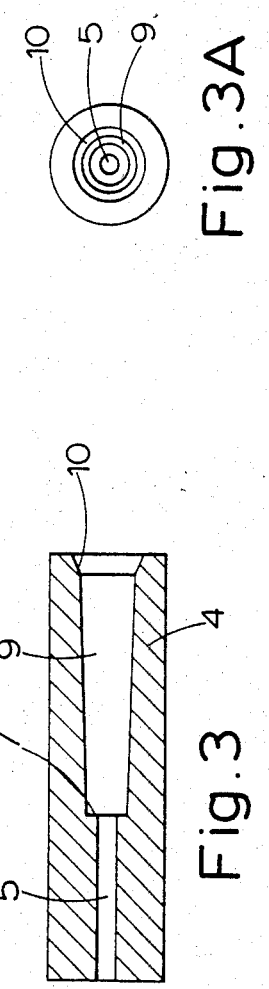
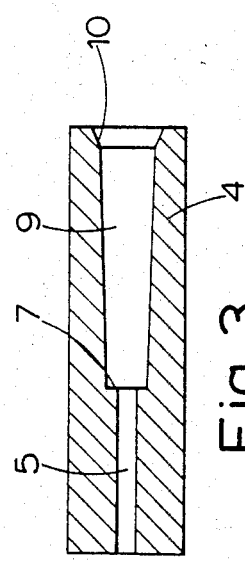

CATHETER ASSEMBLY

CROSS-REFERENCE

This is a continuation of Ser. No. 396,717 filed July 9, 1982, now abandoned which is a continuation of Ser. No. 173,591 filed July 30, 1980, now abandoned.

This invention relates to improvements in a catheter assembly and especially to a reconnecting device for use in such an assembly.

In conventional processes for catheter placement into body spaces, such as the lumen of a blood vessel or epidural space, admission is gained by breaching a wall defining the space with a needle having a hollow bore and an incising forward end, as for example a Tuohy needle. A catheter which by custom comprises a tube made from a flexible elastomeric material with thin walls may then be introduced into the space by either of two methods. Either the catheter tubing may be already in place surrounding the needle with the end just behind the needle point so the catheter tubing follows the needle into the space (the so-called 'needle-inside' assembly) or the catheter tubing may be threaded through the needle after access to the space has been achieved (the so-called 'through the needle' assembly). In either case if the catheter tubing is to remain in place for a long period of time, for example during drip feeding or epidural anaesthesia, it is desirable to remove the needle from the patient and from the catheter tubing. If the needle remains in place movements made by the patient may cause the needle point to damage the tissue of the patient or to the catheter tubing itself. Thus to avoid unnecessary and sometimes harmful restraint to the patient the needle is removed.

In a 'needle-inside' assembly removal of the needle from inside the catheter tubing may cause damage to the catheter walls resulting in the liberation of small particles of catheter material into the blood stream or may even cut through the wall of the catheter tubing thereby releasing administered liquids prematurely. The length of needle required for a conventional cathether is awkwardly long. It is known that attempts to overcome these disadvantages have been made by telescoping the catheter tubing behind the point of the needle or by attaching draw wires to short needles. Both approaches may lead to difficult manipulative processes from removing the needle from the patient in view of not dislodging the catheter tube from its placement and maintaining sterility.

Conventionally, therefore, 'through the needle' assemblies are preferred. However a problem may arise when removing the needle in that conventionally an adaptor such as a female luer site is fixedly carried at the other end of the catheter tubing to enable a connection to be made to a suitable hollow male fitting for communicating with a dispensing container such as a syringe or blood bag. Assemblies have been described to overcome this problem. British Pat. No. 1,123,624 describes a device in which the needle is withdrawn from the patient but not from around the catheter. The danger of damage to the patient or catheter tube by the incising point of the needle is avoided by securing the needle in a protective sheath.

British Pat. No. 1.381.053 describes an assembly in which the needle has lines of weakness along its length which may be cracked open after the placement of the catheter to peel the needle from around the catheter. British Pat. Nos. 1,437,621 and 1,437,622 describe a hollow slotted needle carrying a catheter. After placement of the catheter the slotted needle is withdrawn from the patient and peeled away from the catheter. All these assemblies require manipulation of rigid and flexible components close to the site of injection where the danger is present of accidentally dislodging the emplaced catheter.

Alternatively the catheter end may be left unencumbered and the connecting adapter fitted after catheter placement. British Pat. No. 1,099,496 describes removable end connector in which the catheter is held in a rubber sleeve slightly compressed about the catheter to provide a seal, the connector being adapted to fit to a coaxial member on a syringe by means of for example a screw thread.

British Pat. No. 1,255,086 and U.S. Pat. No. 3,554,580 describes an elastomeric bush used to grip the catheter. The catheter is placed in the bush by threading it through a tube in the bush. The cannula has an outside diameter greater that the internal bore of the bush, thus after removal of the tube from the bush, the bush and catheter form a tight seal. The bush is then formed into a unitary assembly with an adaptor for a dispensing container. This device is not capable of dissassembly and subsequent reassembly.

One form of connector presently used is a blunt hollow needle, the distal end of which is able to be removably placed into the free end of a catheter and the proximal end of which is held in a synthetic polymeric female luer adaptor. In use it is customary to remove the luer adaptor with its associated hollow needle from the catheter, so as to enable removal of the Tuohy needle, and thereafter reconnect the hollow needle within the free end of the catheter tubing.

This reconnection of a small diameter hollow needle inside the bore at the end of a flexible catheter tubing can be manipulatively difficult, especially with an epidural catheterization. The present invention sets out to overcome this manipulative difficulty and the difficulties which occur with the devices described hereinbefore by providing a guide member which facilitates and expedites the reconnection. The assembly has the further advantage that it allows for repetitive reconnection if, for example, a luer fitting needs changing to accommodate different dispensing containers. The device is readily manufactured, disposable and sterilizable.

The present invention provides a catheter assembly which comprises catheter tubing, a hollow needle and a guide member with a longitudinal bore there through for aiding the insertion of the hollow needle into the catheter, which catheter assembly is characterised in that the longitudinal bore in the guide member has a narrower portion and a communicating broader portion, the narrower portion being adapted to receive in close fit the hollow needle and the broader portion being adapted to receive in close fit the catheter; whereby in use the catheter tubing may be positioned for insertion of the hollow needle.

The hollow needle used in this invention will normally and preferably be mounted in a luer female adaptor for attachment to the source of liquid to be eventually passed through the catheter.

In use the catheter tubing is inserted into the guide member as far as it will go, the guide member is gripped firmly and the hollow needle is inserted into the other end of the guide member and pushed in until it projects far enough through the guide member to enter the catheter tubing.

The guide member is made of polymeric material which most aptly is a thermoplastic material such as polyethylene.

Most aptly the broader and narrower portions of the longitudinal bore meet in a shoulder against which the catheter tubing can be held whilst the guide member is being used.

In order to facilitate insertion of the catheter tubing and the hollow needle the one or both ends of the guide member may taper steeply inwards to meet the longitudinal bore, that is the entrance to the guide bore may be countersunk or shaped to provide an easy lead in.

Desirably the guide member is adapted to grasp the catheter tubing when the guide member is compressed between finger and thumb. This may be effected by providing the walls of the guide member with longitudinal slots which extend from the end of the guide member (with the broader portion of the bore) to near the shoulder where the broader and narrower portions of the bore meet. The part of the guide member near the shoulder is preferably incompressible so that the end of the catheter tubing does not become compressed and thus the slots are preferably arranged as one or more opposing pairs.

Most suitably all components of the catheter assembly are provided in sterile form. If desired the catheter assembly may be or form part of a sterile procedure pack.

It will be realized that the longitudinal bore with broader and narrower portions could be considered as two interconnecting bores. From another view the invention accordingly provides an assembly of a length of catheter tubing with the distal end of a hollow needle removably held within the rearward end of the catheter tubing and the hollow needle itself having a connection hub at its proximal end; wherein a guide member has a first longitudinal bore communicating with the rearward end of the guide member, the first longitudinal bore being located around the hollow needle so that the guide member is slidable with respect thereto but leaves the distal end of the hollow needle extending beyond said first longitudinal bore in its assembled position, and said guide member further possessing a communicating second longitudinal bore for accepting the catheter tubing extending back from the forward end of the guide member, the interior end of said second longitudinal bore, where it meets the first longitudinal bore, being of the same dimension as the external diameter of the catheter tubing end; whereby gradual displacement of the guide member in a forward direction relatively to the hollow needle smoothly disconnects the catheter tubing as the hollow needle distal end disappears within the first longitudinal bore; while gradual displacement of the guide member and associated length of catheter tubing held immobile in relation thereto with its free rearward end located as far as possible within the second bore ensures that the hollow needle re-enters the bore of the catheter tubing for smooth reconnection. Of course, the catheter tubing may be located in the guide member before the hollow needle is inserted in its relevant bore, or with the hollow needle already inserted in the first longitudinal bore but not yet protruding into the second longitudinal bore.

To facilitate introduction of the end of the catheter tubing into the guide member, the second longitudinal bore may be tapered inwardly towards the interior of the guide member, provided that a cylindrical bore portion remains within which the tubing can be gripped. Furthermore, a flared portion of steeper taper may be provided where the second longitudinal bore emerges from the forward end of the guide member.

Generally the two bores will be coaxial and there will be a shoulder where the second longitudinal bore of larger diameter meets the first longitudinal bore. It is conceivable but unlikely that the shoulder may be dispensed with if a steeply tapering second longitudinal bore is employed for example to accommodate various sizes of catheter tubing.

In that the hollow needle may be fully removed and replaced in the guide member a tapered portion can also be provided at the end of the first longitudinal bore. If identifiably different from the taper at the end of the second longitudinal bore, no confusion will arise; in any case colour or indicia can be used.

It is preferred for the external shape of the guide member not to follow the internal configuration of the first and second longitudinal bores. The guide member could be cylindrical, but may itself slightly taper from the forward to the rearward end since this assists in one of its modes of use, namely, when the catheter tubing is to be gently disconnected by pushing the guide member. In this shape, moreover, there is a relatively high wall thickness around the first longitudinal bore so that it does not become distorted and prevent smooth movement along the needle.

It will be appreciated that reconnection of the catheter tubing and the hollow needle is greatly facilitated. It is only necessary to push the catheter tubing into the wide end of the second longitudinal bore until it can no longer move, grip the guide firmly between finger and thumb and then slide the catheter tubing and guide member gently in relation to the hollow needle until this protrudes from the end of the first longitudinal bore down inside the catheter tubing.

However, it is often difficult to manipulate in one hand the assembly of the catheter tubing positioned inside the guide member and at the same time introduce the hollow needle with the other hand whilst not simultaneously pushing the catheter tubing out of the guide member. To overcome this drawback it was preferred to develop a guide member which could be held in one hand so as to simultaneously grip and retain the catheter tubing therein.

It is therefore preferred that the guide member be so arranged or constituted as to be capable of gripping the catheter tubing when the hollow needle is being inserted and releasing the catheter tubing at other times.

Generally, this is acheived by distorting the walls of the second longitudinal bore by pressure for example from finger and thumb, so as to grip the catheter tubing. Thus the guide member may be of a resilient elastomeric material for example rubber. It may alternatively or additionally be provided with slots extending longitudinally of, and usually in communication with, the second longitudinal bore. So as to avoid distorting the open end of the catheter tubing when the catheter tube is gripped (and thereby hindering insertion of the hollow needle) the slots preferably extend only part-way back from the forward end of the guide member so as to leave undistorted the region where the second longitudinal bore communicates with the first longitudinal bore. When the finger pressure is removed the catheter tubing is released from the guide member allowing the guide member to slide along the hollow needle.

While the invention as defined above relates to the whole catheter assembly, it will be appreciated that the guide member itself, possessing a first longitudinal bore in communication with second longitudinal bore as defined above, is another separate aspect of the invention.

The invention will be further described with reference to the accompanying drawings, in which:

FIG. 1 shows a longitudinal section through a hub, needle and catheter assembly fitted with a guide member, as assembled prior to use and FIG. 2 is a similar section through the assembly in which the guide member is shown in a position disassembled but immediately before re-connection.

FIGS. 3 and 3A are respectively a longitudinal section and an end view from the right of FIG. 3, of a second embodiment of the guide member capable of gripping the catheter tubing.

Figure 4:
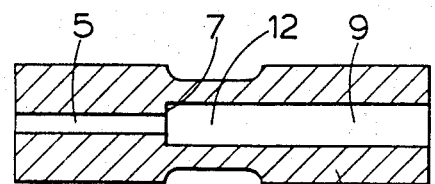
FIGS. 4, 4A; 5, 5A and 6, 6A, 7, 7A are respective sections and end views of third, fourth and fifth embodiments of the guide member.

FIG. 1 shows the free end of flexible catheter tubing 1, attached by a hollow needle 2 held in the free end of the catheter tubing and extending to a hollow metallic or synthetic polymeric hub 3 of characteristic stepped taper as shown for connection to a source of anaesthetic or other fluid. The assembly 1, 2 and 3 is conventional in the art, but according to the present invention there is provided around the hollow needle a guide member 4. This guide member possesses a first longitudinal bore 5 with tapered opening 5a, in which the hollow needle is a snug sliding fit, and a longitudinal second bore 6 with tapered frusto-conical end 6a at the end nearer the catheter tubing 1. This second longitudinal bore 6 terminates in small shoulders 7 at its bottom end. The outer surface of the guide member, as shown, is tapered as at 8 but this is optional and a cylindrical guide works equally as well.

The same features are shown in FIG. 2 but in a slightly different relative position.

The assembly is used as follows. When it is desired to disconnect the catheter tubing 1 from the hollow needle 2, so that the Tuohy needle can be removed from the catheter tubing, the guide member 4 is gripped in its relatively unyielding left-hand portion and moved gently to the right as shown in FIG. 2. The hollow needle can be completely removed from the guide member or can remain in place but retracted, as desired. In either case, this motion serves to gently disengage the free end of the catheter tubing from the free end of the hollow needle, so that the Tuohy needle can be removed as it is passed from the free end of the catheter tubing. To reconnect this assembly the catheter tubing free end is placed exactly as shown in FIG. 2 and the left-hand portion of the guide member is again firmly gripped while also preserving a grip on the free end of the catheter tubing 1 so that their relative positions are unaltered. The hollow needle, guided within the walls of the first longitudinal bore 5, enters the opening at the end of catheter tubing 1 whose extremity has been located within the frusto conical tapered recess and rests on the shoulder 7.

It will be apparent that the assembly shown presents several advantages. Instead of threading a hollow needle of small bore into the opening in the end of free flexible catheter tubing, in which it must fit snugly by friction, the hollow needle is received and retained and guided within a corresponding bore in guide member 4. The catheter tubing only has to be guided into the wide opening of the frusto-conical recess, and it is located for engagement with the hollow needle by its end resting on the shoulder 7 of the guide member.

FIGS. 3, 3A to 6, 6A and 7A show embodiments of this guide member which are adapted to enable the catheter tubing 1 to be gripped and so held in the guide member, whilst the hollow needle 2 is inserted into the end of the catheter tubing 1.

When using the embodiment shown in FIGS. 1 and 2 it is necessary to hold both the free end of the catheter tubing 1 and the guide member 4 in one hand, whilst manipulating the hollow needle 2 in the other hand. It is a relatively difficult operation to hold both the free end of the catheter tubing and the guide member in one hand and to maintain their correct relative positioning—there is a possibility that one or other may be dropped accidentally.

The second, third, fourth, fifth and seventh guide member embodiments are each adapted so that after the catheter tubing 1 has been inserted into the guide member, the catheter tubing is gripped and retained by holding the guide member for example between the thumb and forefinger and squeezing slightly.

FIGS. 3, 3A show a guide member 4 formed of a resilient elastomeric material for example rubber. A longitudinal bore 5 is provided for accepting the hollow needle and a recess 9 for the catheter tubing connects thereto at shoulders 7. The recess 9 may be cylindrical, but is shown slightly tapered inwardly to accommodate variations in catheter tubing diameter. The end of the recess is flared at 10 to facilitate introduction of the catheter tubing. Operation is substantially as before, except that the reconnection is facilitated. Holding the guide member 4 in one hand, the catheter tubing held in the other hand is introduced into recess 9 up to shoulder 7. The guide member is then squeezed for example between thumb and forefinger to distort the resilient material around the recess 9 and so grip the catheter tubing. With the catheter tubing held inside the guide member in one hand, the free hand is used to insert the hollow needle into the open end of the catheter tubing. When the guide member 4 is released the resilient material adopts its original shape so allowing the guide member to be slid along the hollow needle 2.

Figure 4A:
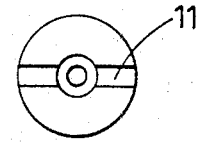

In the embodiment of FIGS. 4, 4A, the guide member 4 is made of a harder plastics material for example polyethylene. However the catheter tubing 1 is gripped by squeezing together the material on either side of a slot 11. The slot 11 extends only part-way along recess 9 so that a portion 12 of the recess is undistorted on squeezing the guide member 4. This avoids distortion of the very end of the catheter tubing 1 when the guide member is squeezed, which might otherwise hinder insertion of the hollow needle 2.

Figure 5:
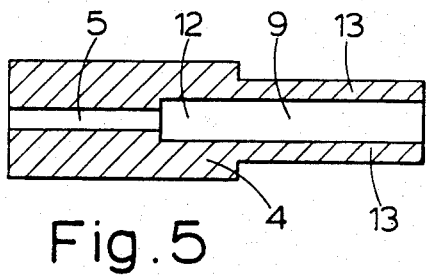
Figure 5A:
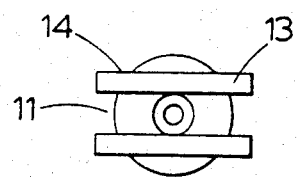

The embodiment of FIGS. 5, 5A also has a slot 11 and undistorted portion 12. However, resiliency is improved by thinning the material on either side of slot 11 to provide flaps 13. The flaps 13 are also provided with a raised surface pattern 14 to act as grips for the finger and thumb.

Figure 6:
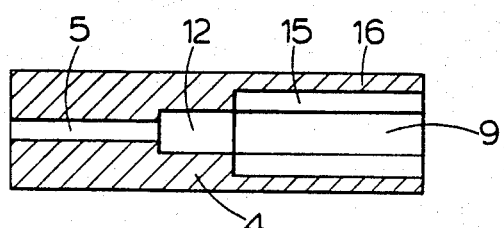
Figure 6A:
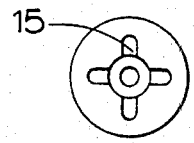

The embodiment of FIGS. 6, 6A is similar in concept to the previous two embodiments, except that it has two intersecting slots 15 each provided with webs 16 at either end. Such a construction facilitates moulding of the guide member in plastics material. Any number of slots may be used to provide the required resiliency.

Various modifications may be made within the scope of the invention defined above. In particular, while the invention has been described with reference to a catheter assembly, any form of manipulatively difficult introduction of one elongate member within the bore of another could be facilitated by a device of the general nature described above.

Figure 7:
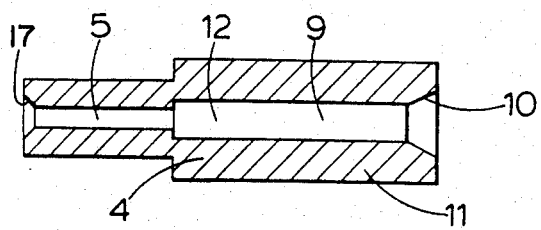
Figure 7A:
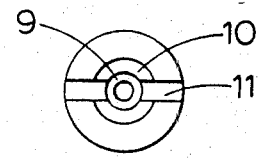

In the embodiment of FIGS. 7 and 7A, the guide member 4 has a slot 11 extending part-way along the recess 9 so that a portion 12 of the recess is undistorted when the catheter tube 1 is gripped by squeezing the guide member 4. At each end of the guide member 4 the recesses 5 and 9 each possess a tapered portion 17 and 10 respectively to aid the location of the hollow needle 2 and catheter tubing 1 in their recesses.

What we claim is:

1. A catheter assembly comprising a hollow needle, a length of catheter tubing with a distal end of said hollow needle removably held within the rearward end of the catheter tubing, the hollow needle itself having a connection hub at its proximal end, and a guide member having a first longitudinal bore communicating with the rearward end of the guide member, the first longitudinal bore being operable to removably fit around the hollow needle so that the guide member is slidable with respect thereto but leaves the distal end of the hollow needle extending beyond said first longitudinal bore in its assembled position, and said guide member further possessing a communicating second longitudinal bore operable to removably accept the catheter tubing extending back from the forward end of the guide member so that the second longitudinal bore of the guide member is slidable with respect to the catheter tubing to permit its removal from the guide member, the second longitudinal bore being of larger diameter than the first longitudinal bore, the interior end of said second longitudinal bore, where it meets the first longitudinal bore, being of the same dimension as the external diameter of the catheter tubing end to thereby form a shoulder in the guide member against which the catheter tubing is held during reconnection, and one or both ends of the guide member has a portion which is steeply tapered inwards to the longitudinal bore to facilitate placement of the hollow needle and catheter tubing into their respective longitudinal bores and wherein the guide member is operable to grasp the catheter by providing the walls of the guide member with longitudinal slots which extend from the end of the guide member (with the broader portion of the bore) to near the shoulder where the broader and narrower portions of the bore meet so as to leave undistorted the region where the second longitudinal bore communicates with the first, narrow longitudinal bore whereby gradual displacement of the guide member in a forward direction relatively to the hollow needle smoothly disconnects the catheter tubing as the hollow needle distal end is retracted within the first longitudinal bore; while gradual displacement of the guide member and associated length of catheter tube held immobile in relation thereto with its free rearward end located as far as possible within the second bore ensures that the hollow needle reenters the bore of the catheter tubing for smooth reconnection.

2. A catheter assembly comprising a hollow needle, a length of catheter tubing with a distal end of said hollow needle removably held within the rearward end of the catheter tubing, the hollow needle itself having a connection hub at its proximal end, and a guide member having a first longitudinal bore communicating with the rearward end of the guide member, the first longitudinal bore being operable to removably fit around the hollow needle so that the guide member is slidable with respect thereto but leaves the distal end of the hollow needle extending beyond said first longitudinal bore in its assembled position, and said guide member further possessing a communicating second longitudinal bore operable to removably accept the catheter tubing extending back from the forward end of the guide member so that the second longitudinal bore of the guide member is slidable with respect to the catheter tubing to permit its removal from the guide member, the second longitudinal bore being of larger diameter than the first longitudinal bore, the interior end of said second longitudnal bore, where it meets the first longitudinal bore, being of the same dimension as the external diameter of the catheter tubing end to thereby form a shoulder in the guide member against which the catheter tubing is held during reconnection, and one or both ends of the guide member has a portion which is steeply tapered inwards to the longitudinal bore to facilitate placement of the hollow needle and catheter tubing into their respective longitudinal bores and wherein the guide member is operable when compressed in the region of the second longitudinal bore to grasp the catheter tubing and hold it immobile in the second longitudinal bore whereby gradual displacement of the guide member in a forward direction relatively to the hollow needle smoothly disconnects the catheter tubing as the hollow needle distal end is retracted within the first longitudinal bore; while gradual displacement of the guide member and associated length of catheter tube held immobile in relation thereto with its free rearward end located as far as possible within the second bore ensures that the hollow needle reenters the bore of the catheter tubing for smooth reconnection.

3. A catheter assembly as claimed in claim 2, wherein the guide member is made from a resilient elastomeric material.

* * * * *